United States Patent
Schmaus et al.

(10) Patent No.: US 7,247,295 B2
(45) Date of Patent: Jul. 24, 2007

(54) USE OF 1,2-DECANDIOL FOR COMBATING GERMS CAUSING BODY ODOR

(75) Inventors: Gerhard Schmaus, Höxter-Bosseborn (DE); Martina Herrmann, Holzminden (DE); Holger Joppe, Dassel (DE)

(73) Assignee: DRAGOCO Gerberding & Co. AG (DE)

( * ) Notice: Subject to any disclaimer, the term of this patent is extended or adjusted under 35 U.S.C. 154(b) by 646 days.

(21) Appl. No.: 10/381,386

(22) PCT Filed: Jun. 19, 2002

(86) PCT No.: PCT/EP02/06751

§ 371 (c)(1),
(2), (4) Date: Mar. 25, 2003

(87) PCT Pub. No.: WO03/000220

PCT Pub. Date: Jan. 3, 2003

(65) Prior Publication Data

US 2003/0195263 A1      Oct. 16, 2003

(30) Foreign Application Priority Data

Jun. 22, 2001  (EP) ................................. 01115131

(51) Int. Cl.
*A61K 7/32* (2006.01)
*A61K 7/00* (2006.01)
(52) U.S. Cl. .......................... 424/65; 424/400; 424/401
(58) Field of Classification Search .................. 424/65, 424/400, 401
See application file for complete search history.

(56) References Cited

U.S. PATENT DOCUMENTS

| | | | | |
|---|---|---|---|---|
| 4,220,665 A | * | 9/1980 | Klein | .......................... 514/739 |
| 6,123,953 A | * | 9/2000 | Greff | .......................... 424/407 |

* cited by examiner

*Primary Examiner*—Shelley A. Dodson
(74) *Attorney, Agent, or Firm*—Akerman Senterfitt; Stephan A. Pendorf

(57) ABSTRACT

The invention relates to a method for inhibiting the growth of organisms causing body odor on a human or animal body. The invention comprises the following step:
  topical application of 1,2-decanediol,
wherein the amount of 1,2-decanediol applied is sufficient to inhibit the growth of organisms forming body odor at the site of application.

7 Claims, 1 Drawing Sheet

USE OF 1,2-DECANDIOL FOR COMBATING GERMS CAUSING BODY ODOR

CROSS REFERENCE TO RELATED APPLICATION

Figure 1:
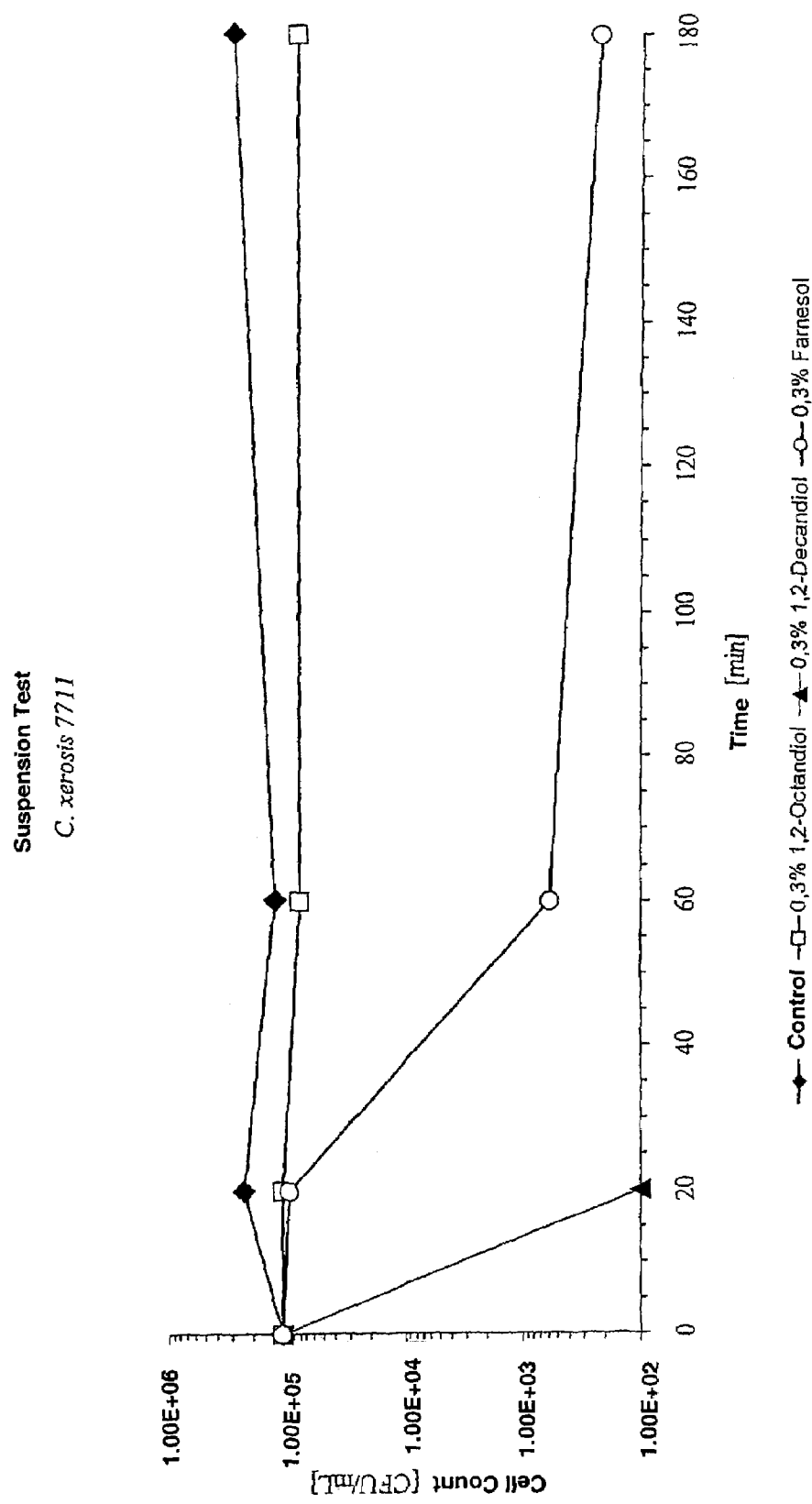

This application is a national stage of PCT/EP02/06751 filed Jun. 19, 2002 and based upon EP 01115131.3 filed Jun. 22, 2001 under the International Convention.

BACKGROUND OF THE INVENTION

1. Field of Invention

The present invention relates to 1,2-decanediol as an agent for inhibiting the growth of organisms causing body odour.

The human skin is populated by a multiplicity of different bacteria. The majority of these bacteria are not pathogenic and irrelevant for the odour of the skin. Others, on the other hand, are capable of decomposing secretions produced by the body, which can result in a more or less strong body odour (in particular underarm and foot odour). The microorganisms which can cause body odour include, in particular, the species listed in the following table.

| Microorganisms | Effect |
| --- | --- |
| Staphylococcus epidermidis | Underarm odour; body odour in general |
| Corynebacterium xerosis | Underarm odour |
| Brevibacterium epidermidis | Underarm odour, foot odour |

Staphylococcus epidermidis, Corynebacterium xerosis and Brevibacterium epidermidis are gram-positive bacteria.

Body odour can be controlled in various ways. With a first control strategy the microbial production of odour substances is not influenced or is influenced to only an insignificant extent, but the odour substances formed are masked by superimposing other fragrances or they are absorbed by absorbents.

In an alternative strategy an attempt is made to prevent the formation of unpleasant odour substances from the start. This aim can be achieved on the one hand by the use of antiperspirants, that is to say by the use of substances which suppress or at least severely inhibit perspiration. On the other hand, the formation of body odour can be controlled by the use of antimicrobial active compounds which, because of their action, destroy, or at least decisively inhibit the reproduction of, the bacteria which lead to the decomposition of secretions produced by the body and thus to the formation of the unpleasant odour substances.

2. Description of the Related Art

A prominent example of an antimicrobial active compound against organisms forming body odour is the substance farnesol; in this context see DE 27 28 921 A1 (corresponds to U.S. Pat. No. 4,220,665) and DE 33 15 058 (corresponds to EP 0 126 944). However, those skilled in the art are also aware of a number of further substances which are already used for the stated purpose.

In the cosmetics industry there is an ongoing demand for alternatives to the antimicrobial active compounds known hitherto for controlling body odour. The aim here is always an antimicrobial substance with the following characteristics:

good effectiveness against the microorganisms responsible for body odour (including underarm odour and foot odour), even in low concentration that is harmless from the dermatological standpoint, toxicologically harmless, good compatibility with the skin, that is to say no production of skin irritations on application of an amount of active compound which kills the microorganisms responsible for body odour or at least inhibits their growth, stability, in particular in the customary cosmetic formulations, and low production costs, that is, to say can be produced using standard methods and/or starting from standard precursors.

The search for a suitable (active) substance that possesses at least the first and, in addition, one or more of the other characteristics mentioned to an adequate degree is made more difficult for the cosmetic specialist in that there is no dependence between the chemical structure of a substance, on the one hand, and its biological activity towards certain organisms (for example the organisms responsible for body odour that have been mentioned above). Equally there is no predictable relationship between the antimicrobial action, toxicological harmlessness, compatibility with the skin and/or the stability.

In the light of this state of affairs, the aim of the present invention was to indicate an antimicrobial active compound that is suitable for inhibiting the growth of organisms causing body odour.

In particular, the active compound to be indicated should be effective against Corynebacterium xerosis, Staphylococcus epidermidis and/or Brevibacterium epidermidis. Moreover, the amount of active compound to be applied topically in order to achieve the desired microbial action should preferably not cause any skin irritation.

The said aims are achieved by indicating 1,2-decanediol as antimicrobial active compound.

In this context the invention is based on the surprising finding that 1,2-decanediol has an excellent action against organisms forming body odour in general, and against Corynebacterium xerosis, Staphylococcus epidermidis, Brevibacterium epidermidis and mixtures of two or more of the said organisms in particular, even when applied in extremely small amounts (concentrations).

Although specialists in the field have already very extensively studied the antimicrobial action of 1,2-diols, which is more or less good in the individual case, hitherto there has been no indication of the outstanding properties of 1,2-decanediol with respect to the particular organisms mentioned. It is also not possible to discern any trend that would have suggested this special effect from the literature.

Thus, although certain indications for the bacteriostatic action of 1,2-decanediol towards certain organisms in relation to the preservation of foods and cosmetics are known from JP-A 51 91327, this publication gives no indications of any antimicrobial action towards the organisms responsible for body odour.

All that is known from JP-A 11 322591 is that certain 1,2-alkanediols having a chain length of 4 to 10 C atoms can be used in order to reduce the dose of conventional antiseptic microbicides in an antimicrobial formulation. 1,2-Pentanediol and 1,2-hexanediol as well as 1,2-octanediol are mentioned as preferred. The Japanese document contains no indication of the action of 1,2-decanediol towards organisms that are responsible for the formation of body odour.

In FR 2 771 632 A1 it is disclosed that certain 1,2-alkanediols having a chain length of 8 to 18 C atoms can be used in a mixture with an N-acylamino acid as an agent against dandruff. Here again 1,2-octanediol is mentioned as preferred.

In U.S. Pat. No. 6,123,953 it is stated that straight-chain 1,2-alkanediols having a chain length of in total 5 to 14 C atoms and preferably 6 to 8 C atoms are suitable for topical application to the skin and in this context in particular for the treatment of acne, for the treatment of capillary layers, for disinfecting minor wounds (scratches) for disinfecting the hands of surgeons and patients as well as for disinfecting the udders of animals giving milk. U.S. Pat. No. 5,123,953 furthermore discloses that formulations that in addition to an alkanediol contain a gel of the glyceryl polymethacrylate type can be used in low concentration for the treatment of acne, skin problems, impetigo, body odours based on microorganisms, "athlete's food (sic)" and the like. In this patent these possible applications are ascribed to a synergistic interaction between the gel and the alkanediol. 1,2-Octanediol is indicated as the preferred alkanediol. The following are mentioned as organisms against which the said combination formulations are effective: *Staphylococcus aureus, Streptococcus faecalis, Pseudomonas aeruginosa, Escherichia coli, Lysteria monocytogenis, Propionibacterium acnes* as well as pathogenic organisms of the species *Lysteria, Staphylococcus, Streptococcus* and *Pseudomonas*. An action of 1,2-decanediol against organisms forming body odour, such as, in particular, *Corynebacterium xerosis, Staphylococcus epidermidis* and/or *Brevibacterium epidermidis* is not disclosed in U.S. Pat. No. 6,123,953.

EP 0 524 548 A1 discloses certain antimicrobially active mixtures which in addition to (A) an antimicrobially active aromatic alcohol of the formula 1

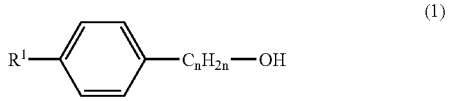

(1)

in which $R^1$ is hydrogen or an alkyl group having 1 to 4 C atoms and n is an integer from 1 to 6, contain (B) an antimicrobially active 1,2- or 1,3-diol of the formula $R^2$—CHOH—$(CHR^3)_x$—$CH_2OH$, where x=0 or 1 and if x=0 $R^2$ is an alkyl group having 6 to 22 C atoms or an alkoxymethyl or 2-hydroxyalkoxymethyl group having, in each case, 6 to 22 C atoms in the alkoxy group, and if x=1 the group $R^2$ is hydrogen and $R^3$ has one of the abovementioned meanings for $R^2$, the components being present in a weight ratio of 9:1 to 1:9. The antimicrobially active mixtures disclosed are said to be suitable for the preparation of skin cleansing agents having an antiseptic action and for the preservation of aqueous preparations of substances that are microbially degradable or perishable. EP 0 524 548 A1 does not contain an indication of the action of 1,2-decanediol against organisms that are responsible for the formation of body odour.

A number of further documents are concerned either with 1,2-decanediol, without disclosing antimicrobial actions of this substance, or are concerned with the action of other 1,2-alkanediols without relating to 1,2-decanediol. To this extent reference is made to the following documents: FR 2 755 371; JP 11 310506; WO 99/11237; WO 99/56715; WO 99/56716; JP 20 0044419; JP 11 335258; JP 10 053510; J. Food Sc. 42(3), 699–701; EP 1 000 542; DE 199 24 496 and JP 20 0148720.

The present invention relates primarily to a method for inhibiting the growth of organisms causing body odour on a human or animal body, the method comprising the topical application of 1,2-decanediol in an amount that is sufficient to inhibit the growth of organisms forming body odour at the site of the application.

Usually 1,2-decanediol is applied in the form of a formulation which in addition to 1,2-decanediol will also contain conventional excipients and, for example, a fragrance or the like. In such a method a formulation containing 1,2-decanediol is applied topically in such a way that the amount of 1,2-decanediol applied with the formulation is sufficient to inhibit the growth of organisms forming body odour at the site of application.

In the present context the finding that an antimicrobially active formulation which contains 1,2-decanediol does not have to contain a gel and in particular does not have to contain glyceryl polymethacrylate gel, as is disclosed in U.S. Pat. No. 6,123,953, is particularly important.

It is equally unnecessary to provide an alcohol of the formula 1,

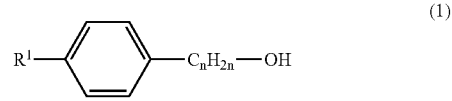

(1)

in which $R^1$ is hydrogen or an alkyl group having 1 to 4 C atoms and n is an integer from 1 to 6, as is disclosed in EP 0 524 548 A1, in such a formulation.

Even in the absence of these substances having a synergistic action, extremely small amounts of 1,2-decanediol are sufficient to inhibit the growth of the said organisms to such an extent that a troublesome odour is no longer developed. In this context the amount of 1,2-decanediol applied will preferably be so small that the 1,2-decanediol does not give rise to any irritation of the skin. Cosmetic formulations which can cause irritation of the skin are virtually precluded from use in the market and therefore, for example in U.S. Pat. No. 6,123,953, particular value was placed on the fact that in the gel/diol substance mixture described in that patent the concentration of diol can be so low that there is no risk of irritation to the skin (cf. U.S. Pat. No. 6,123,953, column 2, lines 9 to 14).

Although 1,2-decanediol already has an excellent action against the said organisms on its own, it is, of course, not precluded to add a further antimicrobial active compound to control these or other organisms. If a further antimicrobial active compound is also present in a formulation in addition to 1,2-decanediol, the formulation is preferably so composed that, compared with a comparison formulation which contains no 1,2-decanediol but otherwise has the same composition, it has an antimicrobial action against *Corynebacterium xerosis, Staphylococcus epidermidis* and/or *Brevibacterium epidermidis* that is increased by a factor of 4 and a MIC value in relation to these organisms that is reduced by at least a factor of 4. The second antimicrobial active compound will thus preferably have only a low activity against the said organisms, but possess high effectiveness against other organisms.

It is pointed out that in the context of the present text, the term 1,2-decanediol comprises both (a) the 2S-configured enantiomer and (b) the 2R-configured enantiomer as well as (c) arbitrary mixtures of 2S- and 2R-configured decanediols. It is true that for commercial reasons it is particularly advantageous to use the racemates of the relevant diols to control the microorganisms forming body odour since these are particularly readily accessible synthetically; however, the pure enantiomers or non-racemic mixtures of these enantiomers are also suitable for the purposes according to the invention.

With a view to formulations according to the invention that contain 1,2-decanediol it is preferred that the concentration of the diol in these formulations is adjusted to a value of between 0.0002 and 20% (m/m). In this context concentrations in the range between 0.02 and 5% (m/m) are preferred.

1,2-Decanediol has only a very weak odour and can therefore also be employed in high concentration in perfume oil compositions. Such perfume oil compositions then have a bacteriostatic action against organisms forming body odour, so that the inherent odour of such a perfume oil composition is retained for longer in the case of topical application. Since the perfume content in a cosmetic finished product is usually only approximately 1% (m/m), a perfume which contains 1,2-decanediol as antimicrobial active compound will preferably consist of approximately 5–50% (m/m) 1,2-decanediol. Use in such high relative concentrations is possible without any problems.

The invention is explained in more detail below with the aid of examples.

Tests to Determine the Antimicrobial Action of 1,2-diols

1. General Test Conditions (MIC Value Determinations)

To prepare various test concentrations 2.6 ml of a 3.3% stock solution (3.3 g 1,2-decanediol or comparison substance in 100 ml ethanol (96% in $H_2O$; Merck, Cat. no. 1.00971)) was used at the starting material in each case. Further test concentrations (diluted sample) in the form of a geometric dilution series were prepared by progressive 2:1 dilution with ethanol (96%; Merck, Cat. no. 1.00971).

Determination of the antimicrobial action of 1,2-decanediol (or of a comparison substance) was carried out with the aid of the agar dilution method based on DIN 58 940/ICS and DIN 58 944/ICS. Petri dishes 5.5 cm in diameter were filled with 8.7 ml freshly prepared Mueller-Hinton agar (Merck, Cat. no. 1.05437 or Wilkins-Chalgren agar boillon (sic), Oxoid, Cat. no. CM 643, supplemented with 10 g agar-agar/litre) kept liquid at 50° C., to which in each case 0.3 ml of the particular sample, that is to say 3.3% (V/V) based on the total volume of agar and sample, was added.

By means of this further dilution of the undiluted stock solution and of the already diluted samples with the test agar (0.3 ml of the stock solution or of the corresponding diluted sample+8.7 ml agar) 30-fold lower end concentrations were prepared in each case (when using the stock solution an initial concentration of 1,100 ppm results). The concentrations given below are based on the pure substance and have been converted to ppm. 2 agar plates were cast per test concentration and nutrient medium.

The following controls were carried out, with 2 agar plates in each case:

TABLE 1

| Controls | |
| --- | --- |
| C1: 9.0 ml Mueller-Hinton agar | (non-inoculated) |
| C2: 8.7 ml Mueller-Hinton agar + 0.3 ml ethanol (96%) | (non-inoculated) |
| C3: 8.7 ml Mueller-Hinton agar + 0.3 ml ethanol (96%) | (inoculated) |
| C4: 9.0 ml Mueller-Hinton agar | (inoculated) |

After solidification and drying (about 1 h at 37° C.), the test plates were inoculated in point form with, in each case, 1 µl of the test organism suspensions listed below. To check purity and identity, the aerobically growing bacteria *Brevibacterium epidermidis*, *Corynebacterium xerosis*; and *Staphylococcus epidermidis* were cultured on Columbia blood agar (BioMérieux, Cat. no. 43049). Further details on the test organisms can be taken from Table 2.

TABLE 2

| Test organisms (strain identities) | |
| --- | --- |
| Test organism | Strain ID |
| *Brevibacterium epidermidis* | ATCC 35514 |
| *Corynebacterium xerosis* | ATCC 7711 |
| *Staphylococcus epidermidis* | ATCC12228 |

The preparation of the test organism suspensions of the test organisms for *Brevibacterium epidermidis*, *Corynebacterium xerosis*, and *Staphylococcus epidermidis* was carried out by incubation of Mueller-Hinton bouillon (Merck, Cat. no. 1.10293), which had been inoculated with a few individual colonies of the particular test organisms, at 36° C. After a distinct turbidity had been achieved, sterile nutrient bouillon was added to the suspensions in such an amount that the turbidity thereof corresponded to McFarland Standard 0.5 (approx. $10^8$ CFU/ml).

The inoculated plates were incubated under the conditions given in Table 3 and were then assessed. The MIC (minimum inhibitory concentration) was considered to be the lowest active compound concentration with which there is macroscopically no growth. Minimum, barely visible growth or a few small individual colonies were assessed as inhibition.

TABLE 3

| Inoculation and incubation | | | | |
| --- | --- | --- | --- | --- |
| Test organism | Strain ID | Growth conditions | Nutrient medium | Incubation |
| *Brevibacterium epidermidis* | ATCC 35514 | aerobic | Mueller-Hinton agar | 18 h at 36° C. |
| *Corynebacterium xerosis* | ATCC 7711 | aerobic | Mueller-Hinton agar | 18 h at 36° C. |
| *Staphylococcus epidermidis* | ATCC 12228 | aerobic | Mueller-Hinton agar | 18 h at 36° C. |

2. MIC Values for 1,2-decanediol Compared with 1,2-octanediol

Suspensions of the microorganisms described above were incubated in accordance with the general test conditions described under 1. and the MIC values of 1,2-decanediol were determined (see Table 4). For reference purposes the MIC values for 1,2-octanediol were also determined.

TABLE 4

| MIC values [ppm] for 1,2-octanediol and 1,2-decanediol | | | |
| --- | --- | --- | --- |
| Test organism | Strain ID | 1,2-Octanediol | 1,2-Decanediol |
| *Staphylococcus epidermidis* | ATCC 12228 | 1800 | 225 |
| *Corynebacterium xerosis* | ATCC 7711 | 3600 | 225 |
| *Brevibacterium epidermidis* | ATCC 35514 | 3600 | 450 |

Comparison of the 1,2-diols shows that the MIC values for 1,2-octanediol are between 3,600 and 1,800 ppm and are thus relatively high. In contrast to this, the MIC values for 1,2-decanediol are distinctly lower.

3. Growth Curve for *Corynebacterium xerosis*—General Test Conditions

Solutions Used:

AC medium: 37 g brain heart infusion, 5 g glucose, 1 ml Tween 80, made up to 1 l with $H_2O$.

Test Substances:
1,2-Octanediol (0.3%)
1,2-Decanediol (0.3%)
Farnesol (0.3%)

Control:
AC medium without active compound

Test Solutions:
Relevant test substance in AC medium

Suspension Test (see FIG. 1)

60 ml AC medium were inoculated with 0.4 ml of a fresh overnight culture of the test organism *Corynebacterium xerosis* (*C. xerosis* 7711). The culture vessel was shaken at 30° C. and 250 rpm until a cell density of $10^5$ to $10^6$ cells/ml had been reached. The test substances were weighed out and in each case dissolved in 2.5 ml AC medium with brief heating to 60° C. The test solutions obtained in this way were then added to 2.5 ml bacterial suspension in each case and the mixtures were incubated for 20, 60 and 180 min maintaining the growth conditions. 100 µl of the incubated test solutions were then taken and the bacterial titre determined by plating-out on nutrient medium.

The growth curves for the test batches described above are shown in FIG. 1.

4. Results (Growth Curves for *Corynebacterium xerosis*)

The growth curve for *Corynebacterium xerosis* (FIG. 1) shows that when used in a concentration of 0.3% 1,2-decanediol has by far the greatest effectiveness of the substances tested. The effectiveness of 1,2-decanediol is even greater than that of farnesol, a known deodorant active compound (see above), which was used as positive control.

5. Determination of the Minimum Inhibitory Concentrations of a Deodorant Pump Spray Formulation Containing 1% Decanediol Compared with a Deodorant Pump Spray Formulation without 1,2-decanediol Pump spray formulations which (a) contained 1,2-decanediol and (b) contained no 1,2-decanediol were tested in accordance with the general test conditions described under 1.

To prepare various concentrations of dilute sample (a) 3 ml of a deodorant pump spray formulation containing 1% (m/m) 1,2-decanediol (composition: ethanol: 10% (m/m), propylene glycol: 5% (m/m), solubilising agent: 2% (m/m), water: 82% (m/m), 1,2-decanediol: 1% (m/m)) and (b) 3 ml of a deodorant pump spray formulation containing no 1,2-decanediol (composition as under (a) but without 1,2-decanediol content and water content increased to 83% (m/m)).

were progressively diluted 2:1 with an ethanol/water mixture (ethanol 96%, Merck, Cat. no. 1.00971; volume ratio ethanol:water=1:9).

Test concentrations in the form of geometric dilution series were prepared in this way.

The determination of the antimicrobial action of the deodorant pump spray formulations containing 1,2-decanediol and containing no 1,2-decanediol was again carried out with the aid of the agar dilution method in accordance with DIN 58 940/ICS and DIN 58 944/ICS. Because of lower concentrations of 1,2-decanediol in the formulations compared with the general test conditions according to point 1 above (1.0% (m/m) instead of 3.3% (m/m)), in these tests petri dishes 5.5 cm in diameter were filled with only 6 ml (instead of 8.7 ml) freshly prepared Mueller-Hinton agar (Merck, Cat. no. 1.05437 or Wilkins-Chalgren agar boillon (sic), Oxoid, Cat. no. CM 643) kept liquid at 50° C., to which the relevant (stock) formulations themselves and also their dilution stages were added (in each case addition of 3 ml, that is to say 33% (V/V) based on the total volume of agar and added formulation).

By means of this further dilution with the test agar (3 ml stock formulation or correspondingly diluted sample plus 6 ml agar), 3-fold lower end concentrations were obtained in each case (when using the stock solution containing 1,2-decanediol an initial concentration of 3333 ppm 1,2-decanediol is obtained). Two agar plates were cast per test concentration and nutrient medium, suspensions of the microorganisms described above were incubated and the MIC values determined. For reference purposes the MIC values of the comparison pump spray formulation without decanediol were also determined. Further details on the MIC value determinations can be taken from point 1.

6. MIC Values of a Deodorant Pump Spray Formulation Containing 1% Decanediol (a) Compared with a Deodorant Pump Spray Formulation Without 1,2-decanediol (b)

Suspensions of the microorganisms described above were incubated in accordance with the general test conditions described under 1. and the MIC values of a deodorant pump spray formulation containing 1% decanediol (a) compared with a deodorant pump spray formulation without 1,2-decanediol (b) were determined (see Table 5).

TABLE 5

| | MIC values [ppm] for 1,2-decanediol | | |
|---|---|---|---|
| Test organism | Strain ID | (a) | (b) |
| *Staphylococcus epidermidis* | ATCC 12228 | 52 | 3333 |
| *Corynebacterium xerosis* | ATCC 7711 | 208 | 1667 |
| *Brevibacterium epidermidis* | ATCC 35514 | 104 | 1667 |

The tests showed that the deodorant pump spray formulations containing 1,2-decanediol (a) show a dramatically increased antimicrobial action against *Corynebacterium xerosis, Staphylococcus epidermidis* and *Brevibacterium epidermidis* compared with formulations which contain no 1,2-decanediol but otherwise have the same composition (b).

The invention claimed is:

1. A method for inhibiting the growth of organisms causing body odour on a human or animal body, having the following step:

applying 1,2-decanediol topically to said human or animal body, wherein the amount of 1,2-decanediol applied is sufficient to inhibit the growth of organisms forming body odour at the site of application, wherein the organisms causing body odour are selected from the group that consists of:
*Corynebacterium xerosis*,
*Staphylococcus epiderimidis*,
*Brevibacterium epidermidis* and
mixtures of two or more of the above-mentioned organisms.

2. A method for inhibiting the growth of organisms causing body odour on a human or animal body, having the following step:
topical application of a formulation containing 1,2-decanediol, wherein the amount of 1,2-decanediol applied by means of the formulation is sufficient to inhibit the growth of organisms forming body odour at the site of application,
wherein the organisms causing body odour are selected from the group that consists of:
*Corynebacterium xerosis*,
*Staphylococcus epiderimidis*,
*Brevibacterium epidermidis* and
mixtures of two or more of the above-mentioned organisms.

3. A method according to claim 2, wherein the formulation does not contain glyceryl polymethacrylate gel.

4. A method according to claim 2, wherein the formulation does not contain an alcohol of the formula 1

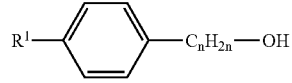

in which $R^1$ is hydrogen or an alkyl group having 1 to 4 C atoms and n is an integer from 1 to 6.

5. A method according to claim 2, wherein the amount of 1,2-decanediol applied is so small that the 1,2-decanediol does not give rise to any skin irritation.

6. A composition effective for inhibiting the growth of organisms causing body odour on a human or animal body, said composition comprising 1,2-decanediol in an amount effective to inhibit the growth on the body of *Corynebacterium xerosis*, *Staphylococcus epiderimidis* and *Brevibacterium epidermidis*.

7. A method according to claim 2, wherein said formulation does not contain gel at all.

* * * * *

UNITED STATES PATENT AND TRADEMARK OFFICE
CERTIFICATE OF CORRECTION

| | |
|---|---|
| PATENT NO. | : 7,247,295 B2 |
| APPLICATION NO. | : 10/381386 |
| DATED | : July 24, 2007 |
| INVENTOR(S) | : Gerhard Schmaus et al. |

It is certified that error appears in the above-identified patent and that said Letters Patent is hereby corrected as shown below:

On the title page: item (73),

Assignee, replace "DRAGOCO Gerberding & Co. AG" with --SYMRISE GmbH & Co. KG --.

Signed and Sealed this

Twenty-eighth Day of August, 2007

JON W. DUDAS
*Director of the United States Patent and Trademark Office*